United States Patent [19]
Adams et al.

[11] Patent Number: 5,262,133
[45] Date of Patent: Nov. 16, 1993

[54] METHOD OF DENUDING SODIUM MERCURY AMALGAM AND PRODUCING SODIUM ALCOHOLATES

[75] Inventors: Robert G. Adams, Niagara Falls; Tilak V. Bommaraju, Grand Island; Sharon D. Fritts, Youngstown, all of N.Y.

[73] Assignee: Occidental Chemical Corporation, Niagara Falls, N.Y.

[21] Appl. No.: 823,402

[22] Filed: Jan. 21, 1992

Related U.S. Application Data

[63] Continuation-in-part of Ser. No. 653,334, Feb. 11, 1991, abandoned.

[51] Int. Cl.[5] .............................................. C01D 13/00
[52] U.S. Cl. .................................. 423/180; 423/192; 568/851
[58] Field of Search .................. 204/99, 128; 423/180, 423/192, 196, 641; 75/388, 389; 562/202, 177; 568/851

[56] References Cited

U.S. PATENT DOCUMENTS

| | | | |
|---|---|---|---|
| 2,336,045 | 12/1943 | Taylor | 204/250 |
| 2,761,880 | 9/1956 | Gerber et al. | 204/94 |
| 3,649,486 | 3/1972 | Proft et al. | 204/99 |
| 4,161,433 | 7/1979 | De Nora et al. | 204/98 |

OTHER PUBLICATIONS

Paseka et al.; Active agents decomposing alkali amalgams; CA 84(6) 36753w; May 1975, Abstract, 1990.

*Primary Examiner*—Kathryn Gorgos
*Attorney, Agent, or Firm*—Wayne A. Jones; Richard D. Fuerle

[57] ABSTRACT

Disclosed is a method of denuding a sodium-mercury amalgam to recover mercury therefrom and produce a sodium alcoholate. The amalgam is reacted with a $C_1$ to $C_4$ alcohol in the presence of a catalyst selected from the group consisting of tungsten carbide, iron treated high density carbon, iridium, ruthenium, and mixtures thereof. The resulting sodium alcoholate is separated from the mercury.

16 Claims, 1 Drawing Sheet

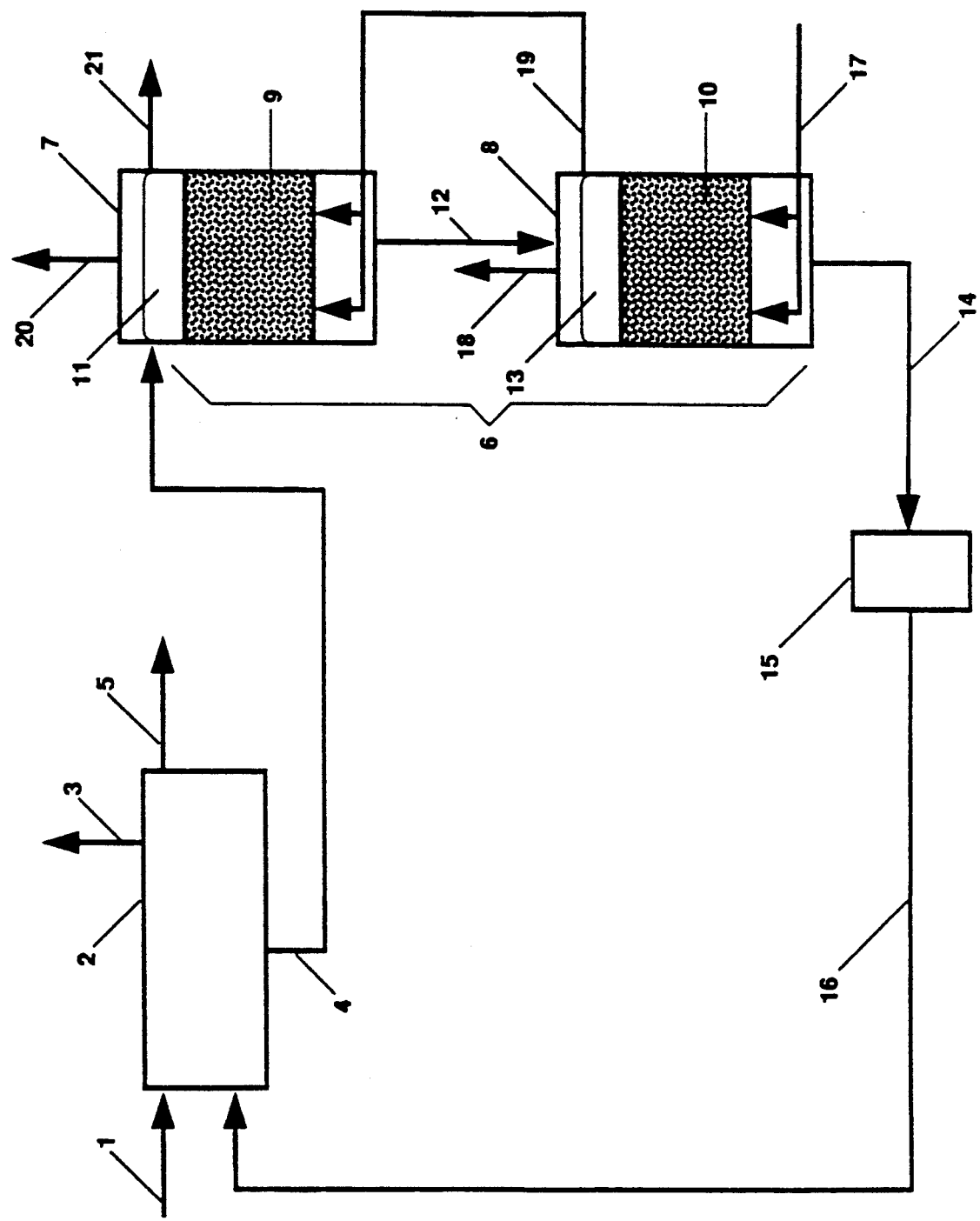

METHOD OF DENUDING SODIUM MERCURY AMALGAM AND PRODUCING SODIUM ALCOHOLATES

This is a continuation-in-part of application Ser. No. 07/653,334, filed Feb. 11, 1991, now abandoned.

BACKGROUND OF THE INVENTION

This invention relates to the denuding of a sodium-mercury amalgam to produce a sodium alcoholate. In particular, it relates to denuding the amalgam using a $C_1$ to $C_4$ alcohol in the presence of a catalyst of tungsten carbide, iron treated high density carbon, iridium, ruthenium, or mixtures thereof.

Sodium methylate, $NaOCH_3$, is of commercial importance in making pharmaceuticals, perfumes, metallic soaps, dyes, and organic intermediates. Sodium methylate can be made as a by-product in the manufacture of chlorine using a mercury chlor-alkali cell. In a mercury chlor-alkali cell, brine is electrolyzed to produce chlorine and a sodium-mercury amalgam. To recover the mercury in the amalgam for reuse in the cell, the amalgam is sent to a denuder where the sodium in the amalgam is stripped from the mercury by either an aqueous process or a methanol process. In the aqueous process, the amalgam flows over a catalyst, such as carbon or carbon mixed with iron or molybdenum, and water reacts with the sodium in the amalgam to form sodium hydroxide according to the equation:

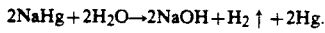

The aqueous process is illustrated in U.S. Pat. No. 4,161,433.

In the methanol process, methanol is used instead of water and sodium methylate is formed instead of caustic:

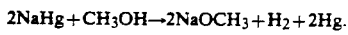

The choice of whether to use the aqueous process or the methanol process depends on whether one wishes to produce caustic soda or sodium methylate, respectively. When the carbon or carbon-molybdenum or carbon-iron catalyst is used in the methanol process, the sodium methylate seems to poison the catalyst so that the efficiency of the denuding reaction falls significantly as sodium methylate is formed. A better catalyst would increase the production of sodium methylate and reduce the cost of making it.

SUMMARY OF THE INVENTION

We have discovered that catalysts of tungsten carbide (WC), iron treated high density carbon, iridium, or ruthenium are very effective in denuding a sodium-mercury amalgam in the methanol process and in similar processes using higher alcohols instead of methanol. We have found that while iron treated low density carbon is prone to erosive deterioration in the methanol process, iron treated high density carbon exhibits prolonged, high activity. Unlike the previous aqueous process catalysts, the catalysts of this invention are very effective in denuding sodium-mercury amalgams in the presence of sodium methylate. Surprisingly, the catalysts of this invention are effective even in a form having a low surface area, and they are expected to be much more effective when they are in a form that has a high surface area. It is also surprising that the catalysts of this invention are effective when used alone and that they do not need to be compounded with other catalysts in order to be effective.

DESCRIPTION OF THE INVENTION

Brief Description of the Drawing

The accompanying drawing is a block diagram illustrating a certain presently preferred embodiment of the process of this invention.

In the drawing, brine passes through conduit 1 into mercury electrolytic cell 2 where it is electrolytically decomposed into chlorine, which passes out through conduit 3, and sodium, which forms a sodium-mercury amalgam. The amalgam leaves through line 4 and spent brine is removed through line 5. The amalgam is sent to denuder 6, which consists of two stages 7 and 8 having beds 9 and 10, respectively. Each bed contains a catalyst according to this invention. The amalgam 11 in stage 7 passes down through bed 9 reacting with alcohol to form mercury. The mixture of amalgam and mercury passes through line 12 into stage 8. There the amalgam 13 remaining in the mixture reacts with alcohol and forms additional mercury. The denuded mercury passes down through bed 10 and out line 14 where pump 15 forces it through line 16 back to electrolytic cell 2. Meanwhile, alcohol from line 17 moves up through bed 10 (stage 8) where it reacts with amalgam 13 that has entered the bed, according to the equation $2NaHg + ROH \rightarrow 2NaOR + H_2 \uparrow + 2Hg$, where R is alkyl to $C_4$. The hydrogen produced leaves through line 18, and the sodium methylate produced leaves with unreacted alcohol through line 19 to stage 7 (bed 9). There, the unreacted alcohol reacts with the amalgam forming hydrogen, which leaves through line 20, and alcoholate, which leaves through line 21.

The process of this invention is applicable to any sodium-mercury amalgam. An amalgam from a mercury chlor-alkali cell typically consists of about 99.4 to about 99.8 wt % mercury and 0.2 to about 0.6 wt % sodium, but the process of this invention is useful with sodium-mercury amalgams of other proportions.

Any alcohol from $C_1$ to $C_4$ can be used in this invention. Examples include methanol, ethanol, propanol, isopropanol, n-butanol, and isobutanol. Methanol is preferred because it reacts more readily and the sodium methylate formed is a valuable product.

The catalysts useful in this invention are tungsten carbide, iron treated high density carbon, iridium, ruthenium, and mixtures thereof. Ruthenium treated carbon, ruthenium and iron treated high density carbon, and iron treated high density carbon are preferred. Ruthenium treated carbon has a high efficiency at a low loading and iron treated high density carbon is inexpensive. Optionally, the catalysts can be used in combination with other catalysts such as cobalt. Because the catalysts are most effective per unit weight when they are in a form having a large surface area, they are preferably mixed with carbon and/or coated onto carbon. The carbon is preferably a high density carbon (i.e., greater than 1.65 gm/cc), such as some forms of graphite. The catalysts can be sprayed onto carbon by plasma or thermal spraying or by thermal decomposition.

The following examples further illustrate this invention.

EXAMPLE 1

Various catalysts and a sodium-mercury amalgam (0.5% Na-99.5% Hg) (20 cc) were preloaded into a 165 cc capacity perfluoroalkoxy reactor connected to a water displacement gas collector. A recorder was used to plot the gas flow from the reactor as sensed by a mass flow meter. A dry ice trap prevented vaporized methanol from entering the gas collector. The apparatus was checked for leaks, the system was purged with nitrogen, the water volume in the gas collector was set for displacement, and the shaker mechanism for the reactor was engaged. The prescribed volume of reactant, either 10 cc of methanol or 12 cc of 15% sodium methylate in methanol, was added over a period of five minutes. At preset intervals, readings were taken of the hydrogen accumulated in the gas collector. At the end of a ten minute test period, the system was shut down. The contents of the reactor were poured into a separatory funnel. A sample of the amalgam was extracted for analysis of percent sodium in mercury. The efficiency of a catalyst, the percentage of the sodium that reacts with the alcohol, was calculated using the formula:

$$\text{Efficiency} = \frac{\text{Liters of hydrogen collected}}{\text{Theoretically expected amount of } H_2 \text{ (in liters)}}$$

$$= \frac{\text{Liters of } H_2 \text{ collected} \times k}{\text{Amalgam wt} \times \text{wt \% of Na in the amalgam}}$$

where $k = 22.4/46$, which is the conversion factor for the 1 mole of $H_2$ or 22.4 liters of $H_2$ generated by 2 mole of Na.

The following table gives the results:

| CATALYST | FE (%) | HARDNESS (SCLEROSCOPE) | SURFACE AREA $m^2/gm$ | EFFICIENCY (%) WITH METHANOL | EFFICIENCY (%) WITH METHANOL & $CH_3ONa$ |
|---|---|---|---|---|---|
| Carbon (Company A) | | | | | |
| $-\frac{1}{2} + \frac{1}{4}$ Inches | 0.5–0.75 | 32.6 | $0.63^a$ | 50 | 25 |
| $-1 + \frac{1}{2}''$ | 0.5–0.75 | 32.6 | $0.37^a$ | 17 | 0.5 |
| $-1 + \frac{1}{2}''$ | 2–3 | 32.6 | $0.9^a$ | 34 | 16 |
| $-\frac{1}{2} + \frac{1}{4}''$ | 2–3 | 32.6 | $0.86^a$ | 60 | 30 |
| Carbon (Company B) | | | | | |
| $-1 + \frac{1}{2}$ Inches | 0.6 | 36–38 | $2.0^b$ | 80–90 | 45 |
| $-\frac{1}{2} + \frac{1}{4}''$ | 0.6 | 36–38 | $2.0^b$ | 90 | 45 |
| WC ($\frac{1}{4}''$ Balls)$^c$ | | | $0.6 \times 10^{-4b}$ | 90 | 63 |
| Stainless Steel Balls ($\frac{1}{4}''$) | | | $1.2 \times 10^{-4b}$ | 13 | |

$^a$Determined by Brunaer Emmett Teller surface area measuring device.
$^b$Determined by calculating the area of the surface of a $\frac{1}{4}''$ sphere.
$^c$Balls were pre-treated with HCl to remove Fe on their surface.

The above table shows that a low density carbon catalyst mixed with various amounts of iron was relatively efficient at the beginning of the denuding reaction, but the efficiency fell off drastically in the presence of sodium methylate. The table further shows that tungsten carbide remained very efficient even in the presence of sodium methylate. In addition, the tungsten carbide was in the form of $\frac{1}{4}''$ balls, and it is expected that the efficiency of tungsten carbide would be much higher in a form having a greater surface area.

EXAMPLE 2

Using the procedure described in Example 1, the efficiency of 10 g of a hydrogen-reduced tungsten carbide on carbon catalyst ($-\frac{1}{2}$ to $+\frac{1}{4}$ mesh size) was compared to the efficiency of 10 g of a high density untreated carbon catalyst ($-\frac{1}{2}$ to $+\frac{1}{4}$ mesh size) in denuding sodium-mercury amalgams in water and methanol. The following table gives the results:

| Catalyst | % Efficiency Water | % Efficiency Methanol |
|---|---|---|
| High density* untreated carbon | 100 | 23 |
| Tungsten carbide on carbon | 100 | 100 |

*1.65 to 1.8 gm/cc

The above table shows that tungsten carbide is required to obtain 100% efficiency in methanol, but is unnecessary to achieve 100% efficiency in water. Therefore, tungsten carbide in methanol is not equivalent to tungsten carbide in water.

EXAMPLE 3

Example 1 was repeated using various types of tungsten carbide catalysts. The following table gives the results.

| Catalyst | Form | % Efficiency In $CH_3OH$ | % Efficiency In 85 wt % $CH_3OH$ – 15 wt % $CH_3ONa$ |
|---|---|---|---|
| 0.3–3 wt % WC + C Blend | $-\frac{1}{2} + \frac{1}{4}$ sieve size | 23–30 | 6 |
| WC Plasma Sprayed On Steel | small strips | 35 | 10 |
| 99.7–99.9 wt % WC + 0.1–0.3 wt % Cobalt Plasma Sprayed On Steel | small strips | 43 | — |
| WC On Low Density 1.6–1.7 gm/cc Carbon $-H_2$ Reduced | $-\frac{1}{2} + \frac{1}{4}$ sieve size | 65 | 23 |
| 99.7–99.9 wt % WC + 0.1–0.3 wt % Cobalt On Low Density 1.6–1.7 gm/cc Carbon $-H_2$ Reduced | $-\frac{1}{2} + \frac{1}{4}$ sieve size | 92 | 38 |
| WC In Cobalt Matrix | $\frac{1}{4}$ inch spheres | 90 | 63 |

The first three catalysts in the above table were ineffective because the tungsten carbide had oxidized to tungsten oxide, $WO_3$.

EXAMPLE 4

Example 1 was repeated using $-\frac{1}{2} + \frac{1}{4}$ sieve size high density (HD) or low density (LD) carbon treated with various catalysts. The following table gives the results.

| Catalyst | Carbon | % Efficiency In $CH_3OH$ | % Efficiency In 85 wt % $CH_3OH$ + 15 wt % $CH_3ONa$ |
|---|---|---|---|
| None | HD | 12 | — |

-continued

| Catalyst | Carbon | % Efficiency In CH$_3$OH | In 85 wt % CH$_3$OH + 15 wt % CH$_3$ONa |
|---|---|---|---|
| Iron | HD | 90 | 60 |
| Iridium | LD | 100 | 63 |
| Ruthenium | HD | 100 | 63 |
| Ruthenium And Iron | HD | 87 | 71 |

The above table shows that without a catalyst very little occurs.

EXAMPLE 5

Example 1 was repeated using either iron treated high density carbon or ruthenium treated low density carbon. The amalgam was reacted with water, methanol, ethanol, n-propanol, or n-butanol. The following table gives the results.

| Reactant | % Efficiency Iron | Ruthenium |
|---|---|---|
| water | 100 | 100 |
| methanol | 90 | 100·1 |
| 5 wt % CH$_3$OH − 15 wt % CH$_3$ONa | 60 | 80 |
| ethanol | 40 | 85 |
| 88 wt % C$_2$H$_5$OH − 12 wt % C$_2$H$_5$ONa | 4 | 50 |
| n-propanol | 40 | 60 |
| 85 wt % C$_3$H$_7$OH − 15 wt % C$_3$H$_7$ONa | — | 8 |
| n-butanol | 10 | 50 |
| 92 wt % C$_4$H$_9$OH − 8 wt % C$_4$H$_9$ONa | — | 6 |

The above table shows that the catalysts are more effective in water than in alcohol, and that the alcoholate poisons the catalysts. While the catalysts are less effective when alcohols other than methanol are used, they are nevertheless effective enough to be useful. Because two reactors can be used (see drawing) and the first reactor contains almost no alcoholate, a high percentage of the sodium in the amalgam is reacted in the first reactor. While the second reactor contains the percentage of alcoholate given in the above table, and therefore a smaller percentage of the sodium in the amalgam is reacted, there is less sodium present to react since much of it has already reacted in the first reactor. The total efficiency achieved from both reactors is therefore higher than the efficiency given in the above table when no alcoholate is present.

We claim:

1. A method for removing sodium from a sodium-mercury amalgam to produce mercury and a sodium methylate comprising
   (A) reacting said amalgam with methanol where a catalyst selected from the group consisting of iron treated high density carbon, iridium treated carbon, ruthenium treated carbon, and mixtures thereof is used, according to the equation $$2NaHg + CH_3OH \rightarrow 2NaOCH_3 + H_2 \uparrow + 2Hg,$$

producing sodium methylate, hydrogen, and mercury; and
   (B) separating said sodium methylate, said hydrogen, and said mercury.

2. A method according to claim 1 wherein said catalyst is iron treated high density carbon.

3. A method according to claim 1 wherein said catalyst is iridium treated carbon.

4. A method according to claim 1 wherein said catalyst is ruthenium treated carbon.

5. A method according to claim 1 wherein said catalyst is formed on a carbon substrate by thermal spraying, plasma spraying, or thermal decomposition.

6. A method according to claim 5 wherein said carbon is graphite.

7. A method according to claim 1 wherein said amalgam comprises about 0.2 to about 0.6 wt % sodium and about 99.4 to about 99.8 wt % mercury.

8. A method according to claim 1 wherein said amalgam and said alcohol move in opposite directions through two reactors, where each reactor contains a bed of said catalyst.

9. A method of removing sodium from a sodium-mercury amalgam and of producing sodium methylate comprising
   (A) passing said through a first bed in a first reactor, then through a second bed in a second reactor, where each bed contains a catalyst selected from the group consisting of high density carbon, iridium treated carbon, ruthenium treated carbon, and mixtures thereof;
   (B) passing methanol in the opposite direction through said second bed in said second reactor, then through said first bed in said first reactor, whereby said methanol reacts with the sodium in said amalgam according to the equation $$2NaHg + CH_{30}OH \rightarrow 2NaOCH_3 + H_2 \uparrow + 2Hg$$

forming mercury, hydrogen, and sodium methylate; and
   (C) separately removing said mercury, hydrogen, and sodium methylate from said first and second reactors.

10. A method according to claim 9 wherein said catalyst is iron treated high density carbon.

11. A method according to claim 9 wherein said catalyst is iridium treated carbon.

12. A method according to claim 9 wherein said catalyst is ruthenium treated carbon.

13. A method according to claim 9 wherein said catalyst is formed on a carbon substrate by thermal spraying, plasma spraying, or thermal decomposition.

14. A method according to claim 9 wherein said carbon is graphite.

15. A method according to claim 9 wherein said amalgam comprises about 0.2 to about 0.6 wt % sodium and about 99.4 to about 99.8 wt % mercury.

16. A method according to claim 9 wherein said amalgam and said alcohol move in opposite directions through two reactors, where each reactor contains a bed of said catalyst.

* * * * *

UNITED STATES PATENT AND TRADEMARK OFFICE
CERTIFICATE OF CORRECTION

PATENT NO. : 5,262,133
DATED : November 16, 1993
INVENTOR(S) : Robert G. Adams et al.

It is certified that error appears in the above-identified patent and that said Letters Patent is hereby corrected as shown below:

Column 1, delete line 39, and substitute -- $2NaHg + 2CH_3OH \rightarrow 2NaOCH_3 + H_2 \uparrow + 2Hg$ --.

Column 2, line 31, delete "+ROH" and substitute -- +2ROH --.

Column 5, line 26, delete "100·1" and substitute -- 100 --.

Column 5, line 27, delete "5" and substitute -- 85 --.

Column 5, delete line 62 and substitute -- $2NaHg + 2CH_3OH \rightarrow 2NaOCH_3 + H_2 \uparrow + 2Hg$ --.

Column 6, delete line 38 and substitute -- $2NaHg + 2CH_3OH \rightarrow 2NaOCH_3 + H_2 \uparrow + 2Hg$ --.

Column 6, line 26, after "said" insert -- amalgam --.

Signed and Sealed this

Thirty-first Day of May, 1994

BRUCE LEHMAN

*Attest:*

*Attesting Officer*     *Commissioner of Patents and Trademarks*